United States Patent [19]

Becker et al.

[11] Patent Number: 4,877,887
[45] Date of Patent: Oct. 31, 1989

[54] PREPARATION OF ALKOXY MALEIC ANHYDRIDES

[75] Inventors: Rainer Becker, Bad Duerkheim; Wolfgang Rohr, Wachenheim, both of Fed. Rep. of Germany

[73] Assignee: BASF Aktiengesellschaft, Ludwigshafen, Fed. Rep. of Germany

[21] Appl. No.: 189,297

[22] Filed: May 2, 1988

[30] Foreign Application Priority Data

May 8, 1987 [DE] Fed. Rep. of Germany ....... 3715344

[51] Int. Cl.[4] .................. C07D 307/56; C07D 307/62
[52] U.S. Cl. .................................... 549/253; 548/544
[58] Field of Search ......................................... 549/253

[56] References Cited

U.S. PATENT DOCUMENTS

| | | | |
|---|---|---|---|
| 3,816,451 | 6/1974 | Crovetti et al. | 548/544 |
| 4,417,028 | 11/1983 | Azevedo | 525/285 |
| 4,582,849 | 4/1986 | Marzolph et al. | 514/425 |

FOREIGN PATENT DOCUMENTS

| | | |
|---|---|---|
| 19296 | 5/1983 | European Pat. Off. . |
| 194037 | 2/1971 | Fed. Rep. of Germany . |
| 193612 | 7/1971 | Fed. Rep. of Germany . |
| 202307 | 7/1971 | Fed. Rep. of Germany . |
| 321765 | 8/1982 | Fed. Rep. of Germany . |
| 3222152 | 12/1983 | Fed. Rep. of Germany . |
| 1280747 | 7/1972 | United Kingdom . |

OTHER PUBLICATIONS

Khan, J. of Pharmaceutical Sciences 73 (12), pp. 1767–1771 (1984).
Rothhaas, Annalen. der Chemie, 501, pp. 295–304 (1933).
Cope, J.A.C.S., 58, pp. 570–572 (1936).
Lynch et al., Journal of Heterocyclic Chemistry, Oct. 1972, pp. 1027–1032.
Relles et al. Journal of Organic Chemistry 37, 3637–45, (1972).

Primary Examiner—Mary C. Lee
Assistant Examiner—Bernard I. Dentz
Attorney, Agent, or Firm—John H. Shurtleff

[57] ABSTRACT

The invention relates to novel alkoxy substituted maleimides of the formula

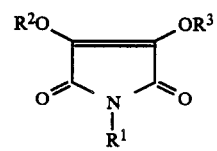

where $R^1$ is hydrogen, $C_1$–$C_8$-alkyl, $C_2$–$C_8$-alkenyl, phenyl or phenylalkyl, and the organic radicals may furthermore carry inert substituents, and $R^2$ and $R^3$ are each $C_1$–$C_4$-alkyl, $C_2$–$C_4$-alkenyl, $C_1$–$C_4$-haloalkyl or $C_2$–$C_4$-haloalkenyl, and alkoxy-substituted maleic anhydrides of the formula II

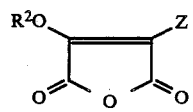

where $R^2$ is $C_1$–$C_4$-alkyl, $C_2$–$C_4$-alkenyl, $C_1$–$C_4$-haloalkyl or $C_2$–$C_4$-haloalkenyl and Z is hydrogen, halogen or a radical $OR^3$, where $R^3$ is $C_1$–$C_4$-alkyl, $C_2$–$C_4$-alkenyl, $C_1$–$C_4$-haloalkyl or $C_2$–$C_4$-haloalkenyl.

The invention further relates to processes for preparing such maleimides I and the corresponding maleic anhydrides II and their use as graft monomers in graft polymers based on polyphenylene ethers.

2 Claims, No Drawings

PREPARATION OF ALKOXY MALEIC ANHYDRIDES

The present invention relates to novel alkoxysubstituted maleimides of the formula

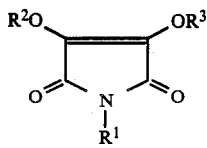

where $R^1$ is hydrogen, $C_1$–$C_8$-alkyl, $C_2$–$C_8$-alkenyl, phenyl or phenylalkyl, and the organic radicals may furthermore carry inert substituents, and $R^2$ and $R^3$ are each $C_1$–$C_4$-alkyl, $C_2$–$C_4$-alkenyl, $C_1$–$C_4$-haloalkyl or $C_2$–$C_4$-haloalkenyl, and novel alkoxy-substituted maleic anhydrides of the formula II

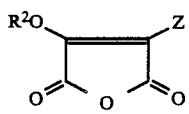

where $R^2$ is $C_1$–$C_4$-alkyl, $C_2$–$C_4$-alkenyl, $C_1$–$C_4$-haloalkyl or $C_2$–$C_4$-haloalkenyl and Z is hydrogen, halogen or a radical $OR^3$, where $R^3$ is $C_1$–$C_4$-alkyl, $C_2$–$C_4$-alkenyl, $C_1$–$C_4$-haloalkyl or $C_2$–$C_4$-haloalkenyl.

The present invention furthermore relates to the preparation of the compounds I and II and their use as graft monomers in graft polymers based on polyphenylene ethers.

J. Heterocycl. Chem. (1972), pages 1027–1032, discloses that alkoxy-sustituted maleimides can be prepared by reacting dichloromaleimides with alcoholates. However, only one halogen atom is exchanged in this reaction. An excess of alcoholate does not lead to substitution of the second halogen atom but to addition at the double bond in accordance with the following equation:

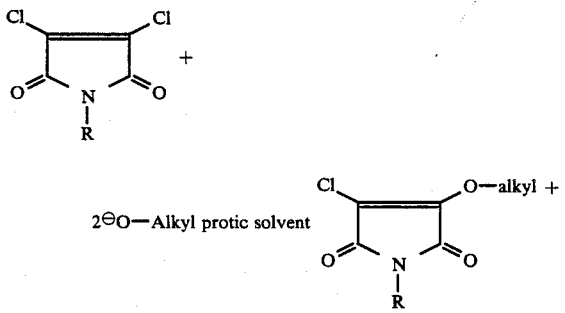

The second halogen atom can be exchanged only using phenolates (cf. J. Org. Chem. 37 (1972), 3637–3645). Dialkoxymaleimides and accordingly also dialkoxymaleic anhydrides are thus not obtainable in this way. Although alkoxy-substituted maleimides and maleic anhydrides are generally mentioned in various publications, for example in German Laid-Open Applications DOS 1,940,370, DOS 1,936,127 DOS 2,023,077 and DOS 3,217,658, European Pat. No. 19,296 and U.S. Pat. No. 3,816,451, no publication contains a characterization of the novel alkoxy-substituted compounds or experimental data on the alleged preparation. It must therefore be assumed that these compounds are purely speculative and have thus not been made available in practice.

It is an object of the present invention to provide the maleic acid derivatives I and II defined at the outset.

Particularly preferred radicals $R^1$ are hydrogen and $C_1$–$C_8$-alkyl, in particular $C_1$–$C_4$-alkyl. $C_2$–$C_8$-alkenyl, phenyl and phenylalkyl are also suitable. The stated radicals may furthermore carry substituents which are inert under the reaction conditions, such as alkyl, alkoxy, haloalkyl, haloalkoxy, preferably of 1 to 4 carbon atoms, halogen, eg. chlorine, bromine or fluorine, nitro or cyano. The following radicals may be mentioned as examples: hydrogen, methyl, ethyl, propyl, isopropyl, n-butyl, isobutyl, sec-butyl, tert-butyl, hexyl, heptyl, octyl, propargyl, chloroallyl, methoxymethyl, methoxyethyl, phenoxyethyl, phenyl, benzyl, phenylethyl, phenylpropyl and phenylbutyl, where the phenyl group in each case may be substituted by, for example, halogen, such as fluorine, chlorine or bromine, alkoxy, such as methoxy or ethoxy, haloalkoxy, such as fluoromethoxy, difluoromethoxy or trifluoromethoxy, alkyl, such as methyl, ethyl or propyl, or haloalkyl, such as trifluoromethyl.

Preferred radicals $R^2$ and $R^3$ in the compounds I and II are straight-chain or branched, unsubstituted or halogen-substituted alkyl radicals of 1 to 4 carbon atoms, eg. methyl, ethyl, propyl, isopropyl, butyl or trifluoromethyl. Furthermore, $R^2$ and $R^3$ may each be $C_2$–$C_4$-alkenyl or haloalkenyl. Halogen substituents are, in particular, fluorine, chlorine or bromine.

In addition to dialkoxy-substituted maleic anhydrides II, monoalkoxy-substituted maleic anhydrides and 3-halo-4-alkoxymaleic anhydrides are also of interest, halogen being, in particular, chlorine or bromine.

We have found that this object is achieved and that the novel maleic acid derivatives can be prepared starting from a dihydroaryliminopyrrole of the formula III

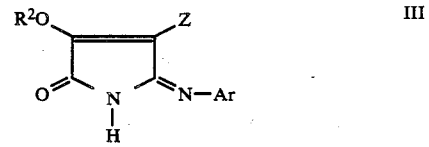

where $R^2$ and Z have the meanings stated in claim 2 and Ar is unsubstituted or substituted aryl, as a key substance. Acidic hydrolysis of III gives the maleimides Ia, which can be converted to the N-alkyl-substituted maleimide in a conventional manner by deprotonation and reaction with an alkylating agent $R^1$-Y. Alkaline hydrolysis of Ia and subsequent acidic cyclization by a conventional method give the desired alkoxy-substituted maleic anhydrides II. These may in turn be converted to N-alkyl- or N-alkylphenyl-substituted maleimides by reaction with primary amines $R^1NH_2$, or to N-phenyl-substituted maleimides by reaction with aniline or a substituted aniline.

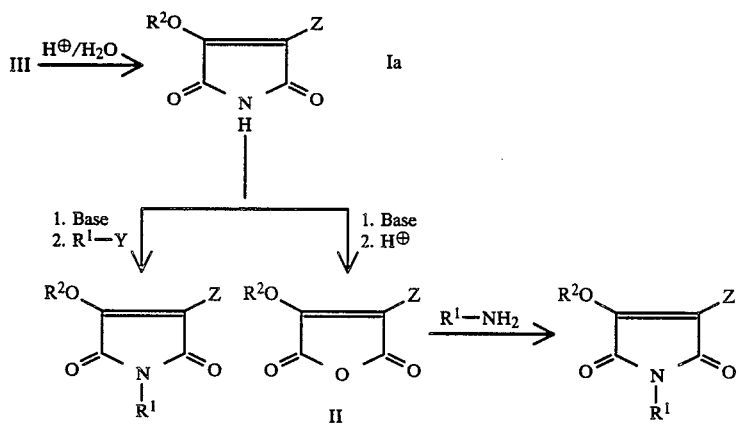

According to German Laid-Open Application DOS 3,308,297, the key substance III is readily obtainable starting from pyridazinones. The aryl radical in III is, for example, phenyl or naphthyl, preferably phenyl. These radicals may carry up to 3 identical or different substituents selected from the grouup consisting of cyano, halogen, $C_1$14 $C_4$-alkyl, $C_1$-$C_4$-alkoxy, $C_1$-$C_4$-haloalkyl and $C_1$-$C_4$-haloalkoxy. Examples of substituted aryl radicals are phenyl, α-naphthyl, β-naphthyl, fluorophenyl, difluorophenyl, chlorophenyl, dichlorophenyl, bromophenyl, dibromophenyl, trichlorophenyl, trifluoromethylphenyl, difluoromethylphenyl, methoxyphenyl, ethoxyphenyl, isopropoxyphenyl, tolyl, difluoromethoxyphenyl, trifluoromethoxyphenyl, tetrafluoroethoxyphenyl and cyanophenyl. These phenyl radicals carry the substituents in the 2-, 3-, 4-, 2,4-, 3,4-, 3,5- or 2,4,6-position.

The acidic hydrolysis of III is advantageously carried out in the presence of an aqueous acid, for example a mineral acid, such as hydrochloric acid, sulfuric acid or phosphoric acid. However, other suitable acids are strong organic acids, such as formic acid or acetic acid. The amount of acid is from 10 to 0.1, in particular from 3 to 1, moles per mole of dihydroaryliminopyrrole III. If necessary, the hydrolysis can be carried out in the presence of an organic solvent, such as low molecular weight alcohols or ethers, eg. tetrahydrofuran, diethyl ether, methanol or ethanol.

The temperature is not particularly critical and may be from 0° to 100° C., preferably from 20° to 50° C. Depending on the reaction temperature, the hydrolysis is complete in the course of a few hours, for example from 1 to 30 hours. At temperatures below 20° C., longer reaction times are required.

The maleimides Ia are isolated in a conventional manner, for example by extraction or by filtering off the solid products and if necessary purifying them by recrystallization.

The conversion of the maleimides Ia to the N-alkyl- or N-alkenyl-substituted compounds is effected in a conventional manner by deprotonating the imides Ia by means of a base and then reacting the product with an alkylating agent. Examples of suitable bases are alkali metal hydroxides, alkaline earth metal hydroxides and alkali metal alcoholates, such as sodium hydroxide, potassium hydroxide, magnesium hydroxide, sodium methylate, potassium ethylate or sodium ethylate. The conventional compounds, such as alkyl halides, in particular chlorides, bromides or iodides, alkyl sulfates, alkyl tosylates or alkyl mesylates, can be used as the alkylating agents $R^1$-Y. The alkylation is carried out in a conventional manner, so that further description is unnecessary.

The preparation of the maleic anhydrides II is carried out by alkaline hydrolysis of the maleimides Ia and cyclization of the maleic acid dianion, formed as an intermediate, in the presence of an acid. If ncessary, the reaction can be carried out in the presence of a water-soluble organic solvent, for example a low molecular weight alcohol or ether. Suitable bases are alkali metal or alkaline earth metal hydroxides or carbonates, eg. sodium hydroxide, sodium carbonate, potassium hydroxide, potassium carbonate or calcium hydroxide. The amount of base is in general from 1 to 3 equivalents, based on maleimide Ia.

The hydrolysis can be carried out at from 0° to 100° C., in particular from 20° to 50° C. When the hydrolysis is complete, the reaction mixture is acidified and the anhydride formed can be isolated in a conventional manner, for example by extraction or by separating it off by filtration.

The conversion of the anhydrides II into maleimides can be carried out in a conventional manner by reacting the anhydrides II with primary amines $R^1NH_2$, where $R^1$ has the meanings stated in claim 1. The reaction can be carried out, for example, as described in German Laid-Open Application DOS 3,222,152, so that further description is unnecessary.

We have found that the novel maleimides I and maleic anhydrides II can be used as monomer components in polymeric systems, in particular as graft monomers in graft polymers based on polyphenylene ethers, with the result that particularly good melt flow in combination with little intrinsic color of the graft polymer is obtained. The graft polymers can be prepared in principle as described in the German Laid-Open Application 3,540,119 or 3,621,207 or in contemporaneous application 37 15 343.9.

Furthermore, the novel compounds I and II can be used as intermediates in organic syntheses, for example for the preparation of dyes, drugs or crop protection agents.

EXAMPLE 1

Preparation of dimethoxymaleimide 500 g of 2,5-dihydro-3,4-dimethoxy-5-phenyliminopyrrol-2-one were stirred with 500 ml of concentrated hydrochloric acid in 2 l of water for 2 days at room temperature. Thereafter, the mixture was cooled and filtered under suction. 325 g of dimethoxymaleimide of melting point 126°–127° C. were obtained.

EXAMPLE 2

Preparation of dimethoxymaleic anhydride 555 g of dimethoxymaleimide in 2 l of 5% strength NaOH were stirred for 2 days at room temperature. Thereafter, the mixture was acidified and extracted thoroughly with methylene chloride. After the organic phase had been separated off and the solvent removed in a rotary evaporator, 486 g of a product of melting point 41°–43° C. remained.

EXAMPLE 3

99 kg of poly-(2,6-dimethyl-1,4-phenylene) ether having a relative viscosity of 0.50, measured in 1% strength by weight chloroform solution at 25° C., and 1 kg of monomer Z were reacted with one another in a twin-screw extruder of the type ZKS 53 (Werner and Pfleiderer) at 270° C. and then devolatilized in a devolatilization zone at 280° C. under reduced pressure. The mean residence time in the extruder was 3.5 minutes. The melt was cooled by passing it through a water bath, and was granulated and dried. The granules were soluble in toluene. The results are summarized in the Table below:

| Monomer Z | Relative viscosity | Color |
| --- | --- | --- |
| Dimethoxymaleic anhydride | 0.55 | pale |
| Dimethoxymaleimide | 0.57 | pale |
| 3-Chloro-4-methoxymaleic anhydride | 0.53 | pale |
| Comparison | | |
| 2-Ethylhexyl monomaleate | 0.64 | pale |

| Monomer Z | Relative viscosity | Color |
| --- | --- | --- |
| No monomer | 0.53 | pale |
| Maleic anhydride | 0.73 | dark |

Comparison with prior art monomers shows the slight increase in viscosity when novel graft monomers are used.

We claim:

1. A process for the preparation of a maleic anhydride

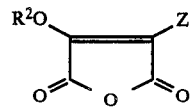

where $R^2$ is $C_1$–$C_4$-alkyl, $C_2$–$C_4$-alkenyl, $C_1$–$C_4$-haloalkyl or $C_2$–$C_4$-haloalkenyl and Z is hydrogen, halogen or a radical $OR^3$, where $R^3$ is $C_1$–$C_4$-alkyl, $C_2$–$C_4$-alkenyl, $C_1$–$C_4$-haloalkyl or $C_2$–$C_4$-haloalkenyl, which comprises:

subjecting a maleimide

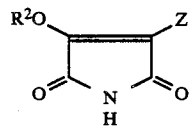

to alkaline hydrolysis at 0° to 100° C. and cyclizing the resulting maleic acid dianion in the presence of an acid to give the anhydride II; and isolating said anhydride II which has been formed in the reaction mixture.

2. A process as claimed in claim 1 wherein the hydrolysis is carried out at a temperature of about 20° to 50° C.